(12) United States Patent
Hart et al.

(10) Patent No.: US 7,670,140 B2
(45) Date of Patent: Mar. 2, 2010

(54) ORTHODONTIC HAND INSTRUMENT FOR DETACHING BRACKETS FROM TEETH

(75) Inventors: Joseph D. Hart, Rancho Cucamonga, CA (US); Joyce C. Ho, Temple City, CA (US); Glenys A. Thorstenson, Azusa, CA (US); William E. Wyllie, II, Pasadena, CA (US); Philip P. Soo, Fullerton, CA (US); John J. Palmer, La Crescenta, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 186 days.

(21) Appl. No.: 11/613,466

(22) Filed: Dec. 20, 2006

(65) Prior Publication Data
US 2008/0153051 A1    Jun. 26, 2008

(51) Int. Cl.
*A61C 3/00* (2006.01)
(52) U.S. Cl. .................................. 433/4; 433/9
(58) Field of Classification Search ............ 433/3, 433/18, 24, 5, 8, 154; 81/300; 140/106, 140/121; D24/153
See application file for complete search history.

(56) References Cited

U.S. PATENT DOCUMENTS

| | | | |
|---|---|---|---|
| 831,477 A * | 9/1906 | Sandall ........................ 7/117 |
| 3,507,043 A | 4/1970 | Rubin | |
| 3,755,902 A | 9/1973 | Northcutt | |
| 3,871,098 A * | 3/1975 | Dean ............................ 433/3 |
| 3,986,265 A | 10/1976 | Cusato | |
| 4,035,919 A * | 7/1977 | Cusato ......................... 433/3 |
| 4,155,164 A * | 5/1979 | White ........................... 433/3 |
| 4,202,328 A | 5/1980 | Sukkarie | |
| 4,248,587 A | 2/1981 | Kurz | |
| 4,455,138 A * | 6/1984 | Sheridan ...................... 433/3 |
| 4,478,576 A * | 10/1984 | Maijer ......................... 433/3 |
| 4,487,580 A * | 12/1984 | Ridgeway .................... 433/3 |
| 4,553,932 A * | 11/1985 | Armstrong et al. ........... 433/4 |
| 4,631,028 A | 12/1986 | Kurz | |
| 4,669,979 A | 6/1987 | Snead | |
| 4,776,791 A | 10/1988 | Hannula et al. | |
| 4,850,864 A | 7/1989 | Diamond | |
| 4,875,855 A * | 10/1989 | Beckett ......................... 433/3 |
| 4,904,183 A | 2/1990 | Hannan et al. | |
| 4,907,965 A * | 3/1990 | Martin ......................... 433/3 |
| 4,921,423 A * | 5/1990 | Kesling ........................ 433/3 |
| 4,950,157 A | 8/1990 | Cleary | |
| 5,035,612 A * | 7/1991 | Martin et al. ................. 433/3 |
| 5,062,793 A | 11/1991 | Cleary et al. | |
| 5,098,288 A | 3/1992 | Kesling | |
| 5,263,859 A | 11/1993 | Kesling | |
| 5,366,372 A | 11/1994 | Hansen et al. | |
| 5,380,196 A | 1/1995 | Kelly et al. | |
| 5,439,379 A * | 8/1995 | Hansen ........................ 433/8 |
| 6,302,688 B1 | 10/2001 | Jordan et al. | |
| 6,382,965 B1 | 5/2002 | Ruiz-Vela et al. | |

(Continued)

*Primary Examiner*—Cris L Rodriguez
*Assistant Examiner*—Heidi M Eide
(74) *Attorney, Agent, or Firm*—Philip P. Soo

(57) ABSTRACT

A hand instrument for detaching orthodontic brackets from a patient's teeth has first jaw, a second jaw and a blade that extends between the first jaw and the second jaw. The blade is received in a channel of a bracket during a debonding procedure, and serves to releasably clamp mesial and distal sections of the bracket to the hand instrument as the sections are detached from the tooth.

15 Claims, 3 Drawing Sheets

U.S. PATENT DOCUMENTS

| | | |
|---|---|---|
| 6,474,988 B1 | 11/2002 | Georgakis et al. |
| 6,582,226 B2 | 6/2003 | Jordan et al. |
| 2005/0123875 A1 | 6/2005 | Stadtmiller et al. |
| 2006/0024634 A1 | 2/2006 | Lai et al. |
| 2006/0024635 A1 | 2/2006 | Lai |
| 2006/0127835 A1 | 6/2006 | Soo et al. |
| 2006/0147868 A1 | 7/2006 | Lai et al. |
| 2007/0122763 A1* | 5/2007 | Farzin-Nia .................... 433/4 |

* cited by examiner

ORTHODONTIC HAND INSTRUMENT FOR DETACHING BRACKETS FROM TEETH

BACKGROUND OF THE INVENTION

1. Field of the Invention

This invention relates to a hand instrument used in orthodontic procedures for removing brackets from teeth. More particularly, the present invention relates to a hand instrument for detaching adhesively bonded orthodontic brackets from teeth as well as methods for detaching orthodontic brackets from teeth.

2. Description of the Related Art

Orthodontic treatment is directed to movement of malpositioned teeth to improved positions in the oral cavity. Orthodontic treatment can greatly enhance the patient's facial appearance, especially in areas near the front of the patient's mouth. Orthodontic treatment can also improve the patient's occlusion so that the teeth function better with each other during mastication.

One type of orthodontic treatment involves the use of a set of appliances and archwires that are commonly known collectively as "braces". During treatment, tiny slotted appliances known as brackets are affixed to the patient's anterior, cuspid and bicuspid teeth, and an archwire is placed in the slot of each bracket. The archwire forms a track to guide movement of the teeth to orthodontically correct positions. Ends of the archwire are often received in the passages of small appliances known as buccal tubes that are affixed to the patient's molar teeth.

In the past, orthodontic brackets were commonly welded or brazed to bands that were placed around the teeth. Today, orthodontic brackets are often bonded directly to the enamel surface of the teeth by an adhesive. Once treatment has been completed, the archwire is removed from the slots of the brackets and each bracket is then removed from the associated tooth.

Orthodontic brackets are typically made of metal, ceramic or plastic. Improved ceramic brackets are described in U.S. Pat. Nos. 5,439,379 and 5,366,372. The ceramic brackets described in those patents have two sections that are spaced apart from each other by a channel. In some of the embodiments described in those patents, the bracket sections are connected to each other by a thin web of material that lies along the bottom of the channel and contacts a layer of adhesive that bonds the bracket to the tooth.

The brackets that are shown in U.S. Pat. Nos. 5,439,379 and 5,366,372 are debonded from the surface of the teeth at the conclusion of treatment by urging the sections in directions toward each other. Hand instruments that are especially useful for debonding such brackets are described in those patents as well as in U.S. Pat. No. 6,474,988. The hand instruments include wall portions for engaging the sides of the bracket so that the sections of the bracket pivot toward each other and away from the tooth surface when handles of the hand instrument are squeezed together.

U.S. Patent Publication No. 2006/0127835 describes another hand instrument for detaching orthodontic brackets from teeth. The hand instrument illustrated in this reference includes two jaws, each of which includes a contact pad for engaging opposite sides of the bracket. When the jaws are moved together, at least a majority of the area of each contact pad is located beneath the archwire slot of the bracket in a lingual direction in order to facilitate fracture of the adhesive bond and release of the bracket from the tooth surface.

Some orthodontic brackets, such as ceramic brackets, are made of materials that are relatively brittle. Consequently, care must be taken during a debonding procedure to ensure that any portions of the bracket that break away from remaining portions of the bracket do not drop into the oral cavity. It can be a time-consuming task for the orthodontic practitioner to find and retrieve loose fragments of brackets that are of a small size, especially when made of translucent or transparent materials.

SUMMARY OF THE INVENTION

The present invention is directed toward an orthodontic hand instrument for debonding brackets that has structure for assisting in the retention of bracket fragments that might otherwise fall into the oral cavity. Specifically, the hand instrument includes a blade that is located between jaws of the hand instrument and is positioned in a channel of the bracket during a debonding procedure. The blade provides a support that serves to help retain fragments of the bracket in secure contact with the hand instrument while sections of the bracket are squeezed together.

In more detail, the present invention in one aspect is directed toward a hand instrument for detaching orthodontic brackets from teeth. The hand instrument comprises a first jaw including a contact pad for engaging a mesial side of a bracket and a second jaw connected to the first jaw for relative movement. The second jaw includes a contact pad for engaging a distal side of the bracket. The hand instrument also includes a blade extending between the first jaw and the second jaw and having an outer end. The outer end is located between the contact pads for reception in a channel of the bracket when the contact pads are in engagement with the sides of the bracket.

Another aspect of the present invention is directed toward an orthodontic assembly that comprises an orthodontic bracket and a hand instrument. The orthodontic bracket includes a mesial section with a mesial side and a distal section with a distal side. The bracket also includes a channel extending between the mesial section and the distal section. The hand instrument includes a first jaw with a contact pad for engagement with the mesial side of the bracket and a second jaw with a contact pad for engagement with the distal side of the bracket. The first jaw is connected to the second jaw for relative movement in directions toward and away from the second jaw. The hand instrument also includes a blade extending between the first jaw and the second jaw, and the blade extends into the channel of the bracket when the contact pads are in engagement with the mesial and distal sides of the bracket.

Another aspect of the present invention is directed toward a method of detaching an orthodontic bracket from a tooth. The method comprises:

placing a blade of a hand instrument in a channel of the bracket that is located between a mesial side of the bracket and a distal side of the bracket;

engaging the mesial side of the bracket with a first jaw of the hand instrument;

engaging the distal side of the bracket with a second jaw of the hand instrument; and urging the first jaw and the second jaw in directions toward each other while the blade remains in the channel.

In preferred embodiments of the invention, the first jaw and the second jaw of the hand instrument are pivotally connected to each other, and the blade is connected to one of the jaws. Preferably, the blade is somewhat flexible and can be moved toward either jaw of the hand instrument during a debonding procedure. Such construction helps ensure that the blade, in combination with the jaws, can firmly clamp onto and grip the bracket sections during a debonding procedure even through the bracket sections may vary in size from one bracket to the next.

These and other aspects of the invention are set out in the description that follows of a preferred embodiment of the invention and are illustrated in the accompanying drawings.

DEFINITIONS

Figure 1:
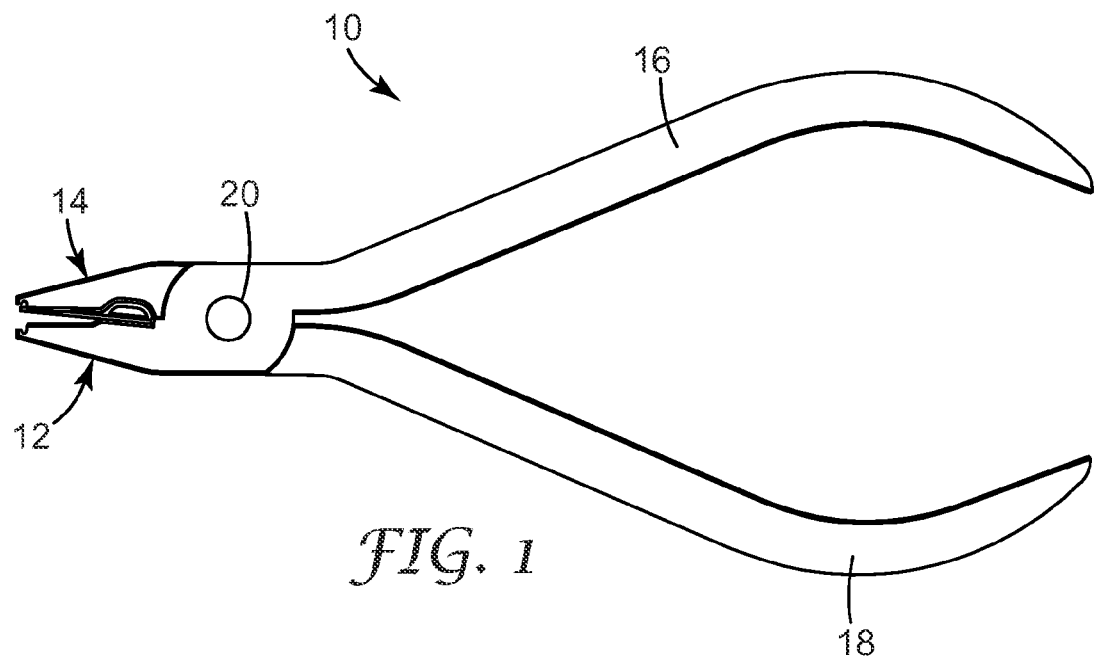
FIG. 1 is a side elevational view of a hand instrument for detaching orthodontic brackets from teeth according to one embodiment of the present invention.

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's cheeks or lips.

"Lingual" means in a direction toward the patient's tongue.

DETAILED DESCRIPTION OF THE PREFERRED EMBODIMENTS

A hand instrument for debonding orthodontic brackets that is constructed according to one embodiment of the invention is illustrated in FIGS. 1-6 and is broadly designated by the numeral 10. The hand instrument 10 includes a first jaw 12 and a second jaw 14. The hand instrument 10 also includes a first handle 16 that is integrally connected to the first jaw 12 and a second handle 18 that is integrally connected to the second jaw 14.

The first jaw 12 is movably connected to the second jaw 14 by a pivot 20. As the handles 16, 18 are squeezed together, the outer tips of the jaws 12, 14 (i.e., the tips of the jaws remote from the handles 16, 18) move toward each other along respective curved paths.

Figure 2:
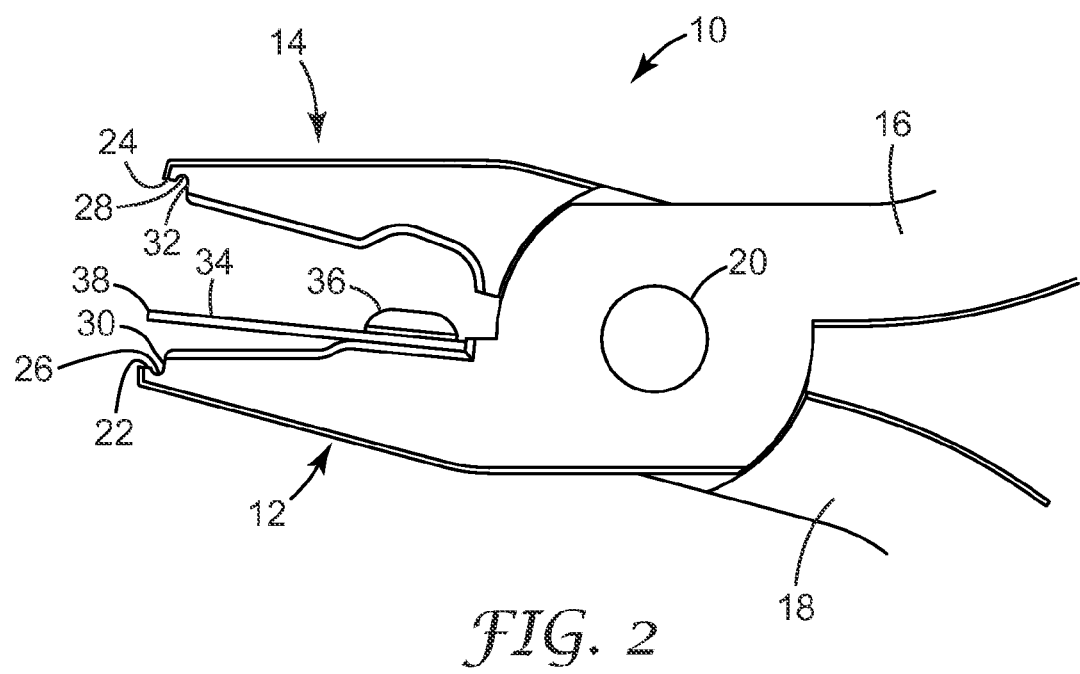
FIG. 2 is an enlarged fragmentary view of a front portion of the hand instrument illustrated in FIG. 1, except that the jaws of the hand instrument are illustrated in an open position.
Figure 3:
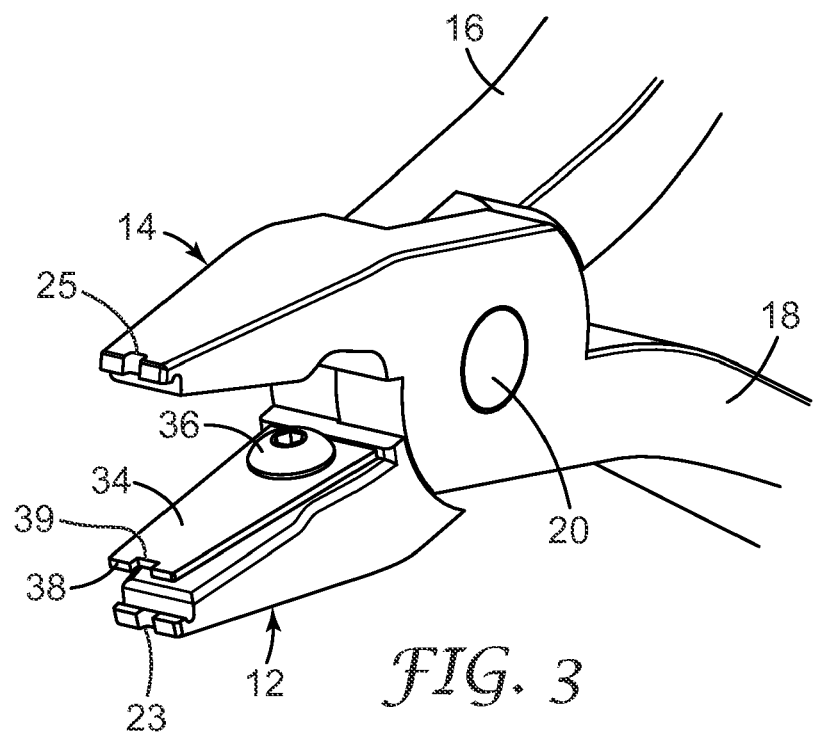
FIG. 3 is an enlarged perspective view of the front portion of the hand instrument shown in FIG. 2.

The outer tips of the jaws 12, 14 are shown alone in enlarged view in FIGS. 2 and 3. As illustrated for example in FIG. 2, the first jaw 12 includes a first contact pad 22 and the second jaw 14 includes a second contact pad 24. Both of the contact pads 22, 24 are elongated and extend in directions parallel to each other and parallel to the pivot axis of the pivot 20.

The first jaw 12 includes a notch 23 that bisects the first contact pad 22. The second jaw 14 includes a notch 25 that bisects the second contact pad 24. The notches 23, 25 each have an overall rectangular shape that is somewhat larger than the cross-sectional configuration of the largest orthodontic archwire that is anticipated for use in treatment. The longer dimension of this rectangular shape extends in a direction parallel to the pivot axis of the pivot 20.

The first jaw 12 also includes a first groove 26 (see, e.g., FIG. 2) that extends alongside the first contact pad 22. The second jaw 14 includes a second groove 28 that extends alongside the second contact pad 24. The contact pads 22, 24 are preferably spaced apart from each other a certain distance when the jaws 12, 14 are fully closed. Moreover, the bottoms of the grooves 26, 28 are spaced apart a distance that is greater than the distance between the contact pads 22, 24 when the jaws 12, 14 are closed.

The first jaw 12 presents a first stop portion 30 (FIG. 2) that extends next to the first groove 26. The second jaw 14 presents a second stop portion 32 that extends next to the second groove 28. When the jaws 12, 14 are fully closed, the stop portions 30, 32 generally extend in a common reference plane that is perpendicular or generally perpendicular to the facing surfaces of the contact pads 22, 24. The stop portions 30, 32 limit the depth of engagement of the jaws 12, 14 in a lingual direction with an orthodontic bracket during a debonding procedure as will be described in more detail in the paragraphs that follow.

The hand instrument 10 also includes an elongated blade 34 that extends along a path between the jaws 12, 14. An inner end of the blade 34 is connected by a fastener or machine screw 36 to an inner face of the first jaw 12 in a location near the pivot 20. As shown in FIGS. 2 and 3, the inner end of the blade 34 includes an innermost edge that is contact with a shoulder formed on the inner face of the jaw 12. The inner face of the second jaw 14 has a recess to provide clearance for the head of the machine screw 36 when the jaws 12, 14 are closed.

The blade 34 also includes an outer end 38 having a notch 39 (FIG. 3). When the jaws 12, 14 are moved to the orientation shown in FIG. 4, the notch 39 of the blade 34 is in alignment with the notches 23, 25 of the jaws 12, 14. The notch 39, similar to the notches 23, 25, has a configuration sufficient to receive the cross-section of the largest orthodontic archwire expected for use.

Optionally, the notch 39 has a somewhat larger configuration than the notches 23, 25. For example, the notch 39 may have a dimension of 0.050 in. (1.3 mm) in a direction parallel to the pivot axis of pivot 20 and a dimension of 0.025 in. (0.6 mm) in a perpendicular direction (i.e., in a direction toward the machine screw 36), while the notches 23, 25 each have a dimension of 0.040 in. (1.0 mm) in a direction parallel to the pivot axis of pivot 20 and a dimension of 0.022 in. (0.6 mm) in a perpendicular direction.

The distance between the outer end of the blade 34 and the pivot 20 is no greater than and is preferably less than the distance between the outer end of the jaws 12, 14 and the pivot 20. Preferably, the blade 34 is made of a flexible material and has sufficient inherent elasticity to self-return to a normally straight orientation when flexed. More preferably, the blade 34 is cut from a sheet of superelastic nickel titanium having a thickness of 0.17 in. (0.4 mm).

Figure 4:
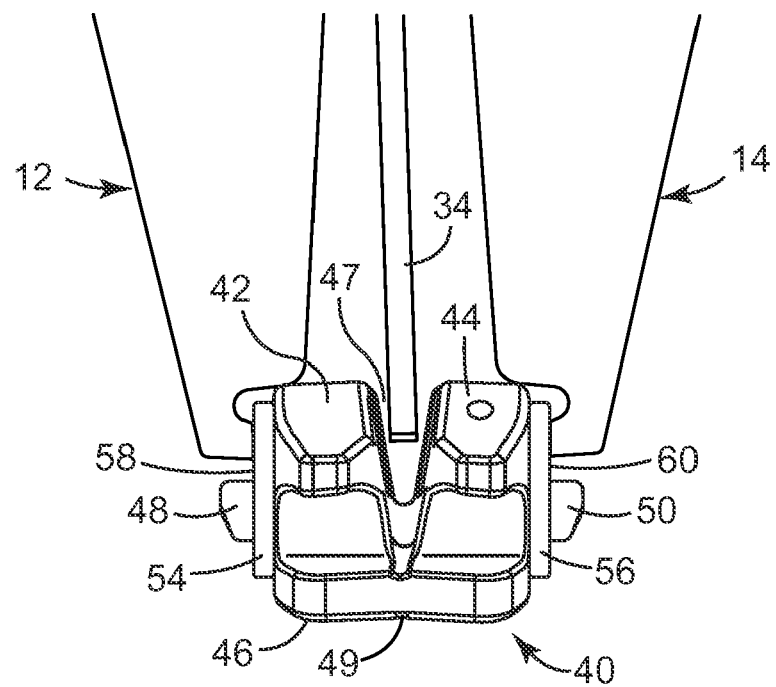
FIG. 4 is an enlarged, fragmentary, side elevational view of the hand instrument shown in FIGS. 1-3 and further showing an exemplary orthodontic bracket, and wherein the jaws of the hand instrument have been moved toward sides of the bracket as might occur during a debonding procedure.
Figure 5:
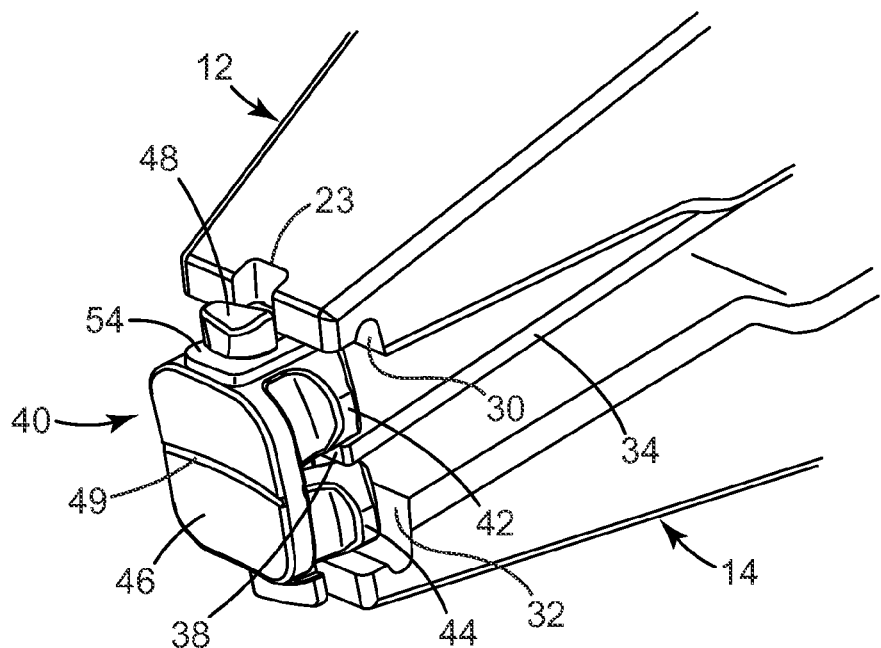
FIG. 5 is a fragmentary, perspective view of the front portion of the hand instrument and the orthodontic bracket shown in FIG. 4, showing the hand instrument and bracket from a different viewpoint.
Figure 6:
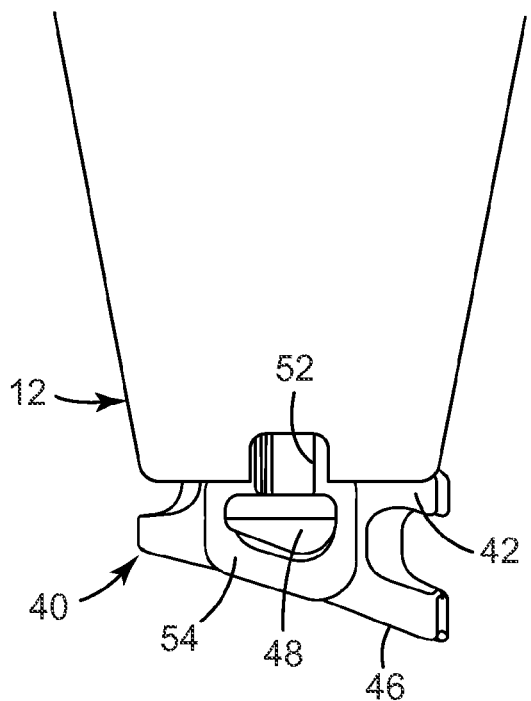
FIG. 6 is a, fragmentary, end elevational view of the front portion of the hand instrument and the orthodontic bracket shown in FIGS. 4 and 5.

FIGS. 4-6 are illustrations of the hand instrument 10, where the front tips of the jaws 12, 14 have been placed next to opposite sides of an exemplary orthodontic bracket 40. In this example, the bracket 40 is a ceramic orthodontic bracket having a mesial section 42 and a distal section 44. Each of the sections 42, 44 includes a base portion, and the two base portions together present a base 46 for bonding the bracket 40 directly to the patient's tooth enamel by an adhesive.

An elongated archwire slot 52 (FIG. 6) extends across the mesial section 42 and distal section 44 of the bracket 40. Optionally, a thin, elongated metallic archwire slot liner defines the archwire slot 52. The archwire slot liner has a generally "U"-shaped cross-sectional configuration and is bonded to the sections 42, 44.

The bracket 40 also includes an elongated debonding channel 47 (see, e.g., FIG. 4) that extends in a generally occlusal-gingival direction between the mesial section 42 and the distal section 44. The channel 47 has a depth in a lingual direction that is equal to or greater than the lingual depth of the archwire slot 52. In addition, the bracket 40 includes a groove 49 (see, e.g., FIG. 5) that extends across the base 46 in a direction parallel to the longitudinal axis of the channel 47.

The bracket 40 is debonded from the tooth by urging the sections 42, 44 toward each other. As the sections 42, 44 are urged together, the bracket 40 detaches from the tooth in the manner described in U.S. Pat. Nos. 5,439,379 and 5,366,372.

The bracket 40 includes a mesial post 48 and a distal post 50 that are integrally connected to the mesial section 42 and the distal section 44 respectively. The posts 48, 50 extend outwardly in opposite directions away from each other. Preferably, each of the posts 48, 50 extends along a reference axis that is parallel to the longitudinal axis of the archwire slot 52. The posts 48, 50 are located in a lingual direction relative to the archwire slot 52, as is shown for post 48 in FIG. 6.

The bracket 40 also includes a latch for releasably retaining an archwire in the archwire slot 52. In the illustrated example, the latch includes a mesial clip 54 that is connected to the mesial post 48 and a distal clip 56 that is connected to the distal post 50.

The clips 54, 56 include resilient side portions that are movable away from each other in order to admit an archwire into the archwire slot 52 when desired. Once the archwire has moved into the archwire slot 52, the side portions of the clips 54, 56 spring back toward each other and retain the archwire in the archwire slot 52. Additional details regarding the clips 54, 56 are set out in the above-mentioned published U.S. Patent Applications nos. 2006/0024634, 2006/0024635 as well as pending U.S. patent application Ser. No. 11/317,346, filed Dec. 23, 2005.

Preferably, the clips 54, 56 are sufficiently stiff to retain an archwire in the archwire slot 52 during the course of treatment so long as the forces exerted by the archwire on the bracket 40 are below a certain minimum value in a generally facial direction (more particularly, in a direction opposite to the direction of insertion of the archwire into the archwire slot 52). However, whenever the forces exerted by the archwire on the bracket 40 in the same direction are greater than the minimum value, as might occur when unexpectedly high forces are encountered, the side portions of the clips 54, 56 move apart from each other to open the clips 54, 56 and release the archwire from the archwire slot 52. Further details regarding such forces are described in U.S. Pat. Nos. 6,302,688 and 6,582,226.

Examples of suitable brackets 40 include the brackets described in the above-mentioned Published U.S. Patent Application Nos. 2006/0024634, 2006/0024635 as well as pending U.S. patent application Ser. No. 11/317,346, filed Dec. 23, 2005. Other ceramic brackets as well as brackets made of polymeric materials or metallic materials may also be used.

The exemplary bracket 40 that is shown in FIGS. 4-6 has a mesial side 58 (FIG. 4) that is represented by the outer side of the mesial clip 54 and a distal side 60 that is represented by the outer side of the distal clip 56. The jaws 12, 14 of the hand instrument 10 are illustrated in FIGS. 4-6 in positions adjacent the bracket sides 58, 60 and as they might appear immediately before detaching the bracket 40 from the patient's tooth. More specifically, the first contact pad 22 of the first jaw 12 is adjacent the mesial side 58 and the second contact pad 24 of the second jaw 14 is adjacent the distal side 60.

The stop portions 30, 32 are constructed to engage the facial sides of the mesial and distal sections 42, 44 respectively when the hand instrument 10 is fully seated over the bracket 40. This fully seated arrangement preferably is carried out while positioning the jaws 12, 14 in such a manner that the notches 23, 25, 39 are aligned with the archwire slot 52. This position of the jaws 12, 14 helps ensure that the contact pads 22, 24 will have flat and substantial engagement with the clips 54, 56 respectively during a debonding procedure.

Optionally, the hand instrument 10 may be used to debond the bracket 40 during the time that an archwire is received in the archwire slot 52. The notches 23, 25, 39 are constructed to receive the archwire when the notches 23, 25, 39 are aligned with the archwire slot 52 and the hand instrument 10 is seated over the bracket 40 as described in the previous paragraph. Such construction enables the bracket 40 to remain connected to the archwire after the debonding procedure is completed. Notches such as the notches 23, 25, 39 are particularly advantageous when provided for all of the brackets of a dental arch since the archwire can serve as a convenient means to simultaneously grip and retain all of brackets and all of the brackets can be removed at once from the oral cavity upon completion of the debonding procedure.

During use of the hand instrument 10 with the bracket 40, the handles 16, 18 are squeezed together to engage the contact pads 22, 24 with the clips 54, 56. As the handles 16, 18 continue to move about the pivot axis of pivot 20, the contact pads 22, 24 each move in a direction toward the blade 34 and bear against the clips 54, 56 such that the sections 42, 44 are urged in directions toward each other. As a result, one or both of the sections 42, 44 pivot in direction(s) toward each other in an arc and about a reference axis that is generally parallel to the longitudinal axis of the channel 47.

Preferably, the space between the outer end 38 of the blade 34 and the contact pad 22 when the blade 34 is relaxed is greater than the distance between the mesial and distal sides of the bracket section 42. Consequently, as the handles 16, 18 are closed, the jaw 14 tends to contact the bracket section 44 before the jaw 12 contacts the bracket section 42. As the handles 16, 18 continue to move toward each other, the jaw 14 pushes against the distal side of the section 44 and causes the jaw 12 to further move toward the bracket 40. The blade 34 flexes during such movement until the space between the mesial side of the section 42 and the contact pad 22 is eliminated, such that the section 42 is now secured between the blade 34 and the jaw 12 while the section 44 is secured between the blade 34 and the jaw 14.

As one or both of the sections 42, 44 pivot(s), the thin web of bracket material that is located between the channel 47 and the groove 49 fractures, enabling the base portions associated with the section(s) 42, 44 to detach from underlying areas of the patient's tooth. However, so long as the jaws 12, 14 remain fully closed (i.e., to the extent of possible movement while gripping the bracket 40), the sections 42, 44 remain in secure engagement with the combination of the blade 34 and the contact pads 22, 24. Specifically, the mesial and distal sides of the mesial section 42 are clamped between the blade 34 and the contact pad 22, and the mesial and distal sides of the distal section 44 are clamped between the blade 34 and the contact pad 24.

Often, both sections 42, 44 will have detached from the patient's tooth by the time that jaws 12, 14 have reached the extent of possible movement toward each other and the sections 42, 44 are clamped between the contact pads 22, 24 and the blade 34. However, if only one of the sections 42, 44 has detached from the patient's tooth by the time that the jaws 12, 14 have reached the extent of possible movement toward each other, the hand instrument 10 can be rocked by the practitioner about a reference axis generally parallel to the longitudinal axis of the channel 47 while the sections 42, 44 continue to be clamped in order to detach the remaining section.

After both of the sections 42, 44 have been debonded from the tooth, the hand instrument 10 is removed from the patient's oral cavity. The practitioner can then move the handles 16, 18 apart in order to release the sections 42, 44 from the jaws 12, 14 and the blade 34.

The blade 34 represents a significant advantage, in that it provides a support that facilitates grasping of the sections 42, 44. The blade 34 is especially advantageous when used with certain ceramic brackets that have a channel between sections that is somewhat "V"-shaped in cross-sectional view. For example, the facing inner walls of the sections 42, 44 as shown in FIG. 4 are inclined in opposite directions, which might cause the sections 42, 44 to slip out of the grip of jaws if the practitioner instead used a pliers-type hand instrument that lacked a blade similar to blade 34.

Moreover, the flexible characteristics of the blade 34 facilitate grasping of the sections 42, 44 and use of the hand instrument 10 with a variety of brackets of different sizes. The flexible blade 34 enables the space between the outer end 38 and the contact pad 22 to be sufficiently large for straddling the section 42 with little or no resistance or tight engagement when the handles 16, 18 are opened. In addition, if the mesial-distal width of the bracket sections varies from the width shown in the drawings, the blade 34 can flex as needed in order to close such space when the handles 16, 18 are closed.

In addition, the use of nickel-titanium for making the blade 34 is also an advantage because such material is less likely to be deformed past its yield point during a debonding operation than other materials such as stainless steel. Nickel-titanium is less likely to crimp or be permanently deformed in instances, for example, when the bracket fractures in an unusual manner or in instances when the hand instrument is accidentally dropped onto the floor.

The hand instrument 10 may also be used to debond brackets made of metallic or polymeric materials. In these instances, the web of material below the channel (such as channel 47) may not fracture but instead flex and retain the mesial and distal sections coupled together. However, debonding may still be carried out in a manner similar to the debonding methods described above.

All of the patents and patent applications identified above are hereby expressly incorporated by reference herein. Those skilled in the art will recognize that other options, alternatives and additions are possible to the hand instrument set out above without departing from the essence of our invention. For example, the blade of the hand instrument may retract in a direction toward the pivot when the handles of the hand instrument are opened. Accordingly, the invention should not be deemed limited to the specific embodiments described in detail above, but instead only by a fair scope of the claims that follow along with their equivalents.

The invention claimed is:

1. A hand instrument for detaching orthodontic brackets from teeth comprising:
    a first jaw including a contact pad for engaging a mesial side of a bracket;
    a first handle connected to the first jaw;
    a second jaw connected to the first jaw for relative movement, the second jaw including a contact pad for engaging a distal side of the bracket;
    a second handle connected to the second jaw, wherein the second jaw is pivotally connected to the first jaw, and wherein the first jaw and the second jaw move toward each other as the first handle and the second handle are squeezed together; and
    a blade extending between the first jaw and the second jaw and having an outer end, the outer end being located between the contact pads for reception in a channel of the bracket when the contact pads are in engagement with the sides of the bracket, wherein the blade is flexible and wherein the outer end of the blade includes a notch.

2. A hand instrument according to claim 1 wherein the blade comprises an alloy of nickel and titanium.

3. A hand instrument according to claim 1 wherein the blade is connected to the first jaw.

4. A hand instrument according to claim 1 wherein the first jaw and the second jaw are movable toward each other to a closed position, and wherein the blade has an overall length that is no greater than the length of the first jaw and the second jaw when the jaws are in the closed position.

5. A hand instrument for detaching orthodontic brackets from teeth comprising:
    a first jaw including a contact pad for engaging a mesial side of a bracket;
    a second jaw connected to the first jaw for relative movement, the second jaw including a contact pad for engaging a distal side of the bracket; and
    a blade extending between the first jaw and the second jaw and having an outer end, the outer end being located between the contact pads for reception in a channel of the bracket when the contact pads are in engagement with the sides of the bracket, wherein the outer end of the blade includes a notch, and wherein the first jaw and the second jaw each include an outer end having a notch that is aligned with the notch of the blade.

6. A hand instrument according to claim 5 wherein the second jaw is pivotally connected to the first jaw.

7. A hand instrument according to claim 6 wherein the blade is connected to the first jaw.

8. An orthodontic assembly comprising:
    an orthodontic bracket including a mesial section with a mesial side and a distal section with a distal side, the bracket also including a channel extending between the mesial section and the distal section; and
    a hand instrument including a first jaw with a contact pad for engagement with the mesial side of the bracket and a second jaw with a contact pad for engagement with the distal side of the bracket, the first jaw being connected to the second jaw for relative movement in directions toward and away from the second jaw, the hand instrument also including a blade extending between the first jaw and the second jaw, and wherein the blade extends into the channel of the bracket when the contact pads are in engagement with the mesial and distal sides of the bracket, wherein the outer end of the blade includes a notch, and wherein the first jaw and the second jaw each include an outer end having a notch that is aligned with the notch of the blade.

9. An assembly according to claim 8 wherein the blade is flexible.

10. An assembly instrument according to claim 9 wherein the blade comprises an alloy of nickel and titanium.

11. An assembly instrument according to claim 8 wherein the blade is connected to the first jaw.

12. An assembly instrument according to claim 8 wherein the first jaw and the second jaw are movable toward each other to a closed position, and wherein the blade has an overall length that is no greater than the length of the first jaw and the second jaw when the jaws are in the closed position.

13. An assembly instrument according to claim 8 wherein the second jaw is pivotally connected to the first jaw.

14. An assembly instrument according to claim 13 wherein the blade is connected to the first jaw.

15. A method of detaching an orthodontic bracket from a tooth comprising:

placing a blade of a hand instrument in a channel of the bracket that is located between a mesial side and a distal side of the bracket;

engaging the mesial side of the bracket with a first jaw of the hand instrument;

engaging the distal side of the bracket with a second jaw of the hand instrument; and urging the first jaw and the second jaw in directions toward each other while the blade remains in the channel, wherein the act of urging the first jaw and the second jaw in directions toward each other is carried out until the bracket fractures and wherein the blade flexes such that the mesial side of the bracket is secured between the blade and the first jaw while the distal side of the bracket is secured between the blade and the second jaw.

\* \* \* \* \*

UNITED STATES PATENT AND TRADEMARK OFFICE
CERTIFICATE OF CORRECTION

PATENT NO. : 7,670,140 B2
APPLICATION NO. : 11/613466
DATED : March 2, 2010
INVENTOR(S) : Hart et al.

It is certified that error appears in the above-identified patent and that said Letters Patent is hereby corrected as shown below:

Column 9
Line 3, Claim 10, After "assembly", delete "instrument".
Line 5, Claim 11, After "assembly", delete "instrument".
Line 7, Claim 12, After "assembly", delete "instrument".
Line 12, Claim 13, After "assembly", delete "instrument".
Line 14, Claim 14, After "assembly", delete "instrument".

Signed and Sealed this

Twenty-seventh Day of April, 2010

David J. Kappos
*Director of the United States Patent and Trademark Office*